(12) United States Patent
Prylutskyy et al.

(10) Patent No.: US 11,771,339 B2
(45) Date of Patent: Oct. 3, 2023

(54) HETERODYNE CATHETER CALIBRATION SYSTEM

(71) Applicant: Biosense Webster (Israel) Ltd., Yokneam (IL)

(72) Inventors: Aleksander Prylutskyy, Migdal Ha'emek (IL); Vadim Gliner, Haifa (IL); George Gusein, Akko (IL); Ilan Goldenberg, Netanya (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 205 days.

(21) Appl. No.: 17/362,725

(22) Filed: Jun. 29, 2021

(65) Prior Publication Data
US 2022/0409087 A1 Dec. 29, 2022

(51) Int. Cl.
*A61B 5/00* (2006.01)
*A61B 5/06* (2006.01)
*A61B 5/1495* (2006.01)
*A61B 5/145* (2006.01)

(52) U.S. Cl.
CPC ............ *A61B 5/062* (2013.01); *A61B 5/1495* (2013.01); *A61B 5/6852* (2013.01); *A61B 5/065* (2013.01); *A61B 5/14503* (2013.01); *A61B 2560/0223* (2013.01); *A61B 2562/0223* (2013.01)

(58) Field of Classification Search
None
See application file for complete search history.

(56) References Cited

U.S. PATENT DOCUMENTS

| | | |
|---|---|---|
| 3,644,825 A | 2/1972 | Davis, Jr. et al. |
| 3,868,565 A | 2/1975 | Kuipers |
| 4,017,858 A | 4/1977 | Kuipers |
| 4,054,881 A | 10/1977 | Raab |
| 4,849,692 A | 7/1989 | Blood |

(Continued)

FOREIGN PATENT DOCUMENTS

| | | |
|---|---|---|
| KR | 100403378 B1 | 2/2004 |
| WO | 1994004938 A1 | 3/1994 |
| WO | 1996005768 A1 | 2/1996 |

OTHER PUBLICATIONS

EP Application No. 22181456.9-1122—Extended European Search Report dated Oct. 19, 2022.

*Primary Examiner* — Christopher Koharski
*Assistant Examiner* — Michael S Kellogg
(74) *Attorney, Agent, or Firm* — Louis J. Capezzuto

(57) ABSTRACT

A catheter calibration system includes a calibration chamber, a receiver and a processor. The calibration chamber is configured to generate a calibration magnetic field that oscillates at a first frequency. The calibration chamber includes a cavity for inserting a distal end of a catheter having one or more magnetic-field sensors. The receiver is configured to be connected to the catheter, to receive from the catheter one or more signals, which are generated by the one or more magnetic-field sensors in response to the calibration magnetic field, and to convert the one or more signals into one or more respective intermediate frequency (IF) signals having a second frequency that is lower than the first frequency. The processor is configured to receive the one or more IF signals from the receiver and to calculate catheter navigation calibration data from the one or more IF signals.

8 Claims, 5 Drawing Sheets

(56) References Cited

U.S. PATENT DOCUMENTS

| | | | |
|---|---|---|---|
| 5,042,486 A | 8/1991 | Pfeiler | |
| 5,103,174 A | 4/1992 | Wandass et al. | |
| 5,391,199 A | 2/1995 | Ben-Haim | |
| 5,442,583 A | 8/1995 | Kirk et al. | |
| 6,239,724 B1 | 5/2001 | Doron et al. | |
| 6,266,551 B1 * | 7/2001 | Osadchy | A61B 5/062 600/424 |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 6,810,240 B2 | 10/2004 | Doing et al. | |
| 8,587,304 B2 | 11/2013 | Budker et al. | |
| 10,148,282 B1 * | 12/2018 | Govari | H03M 3/352 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2007/0123778 A1 | 5/2007 | Kantorovich | |
| 2011/0152703 A1 | 6/2011 | Zuckerman et al. | |
| 2021/0038284 A1 | 2/2021 | Gliner et al. | |

\* cited by examiner

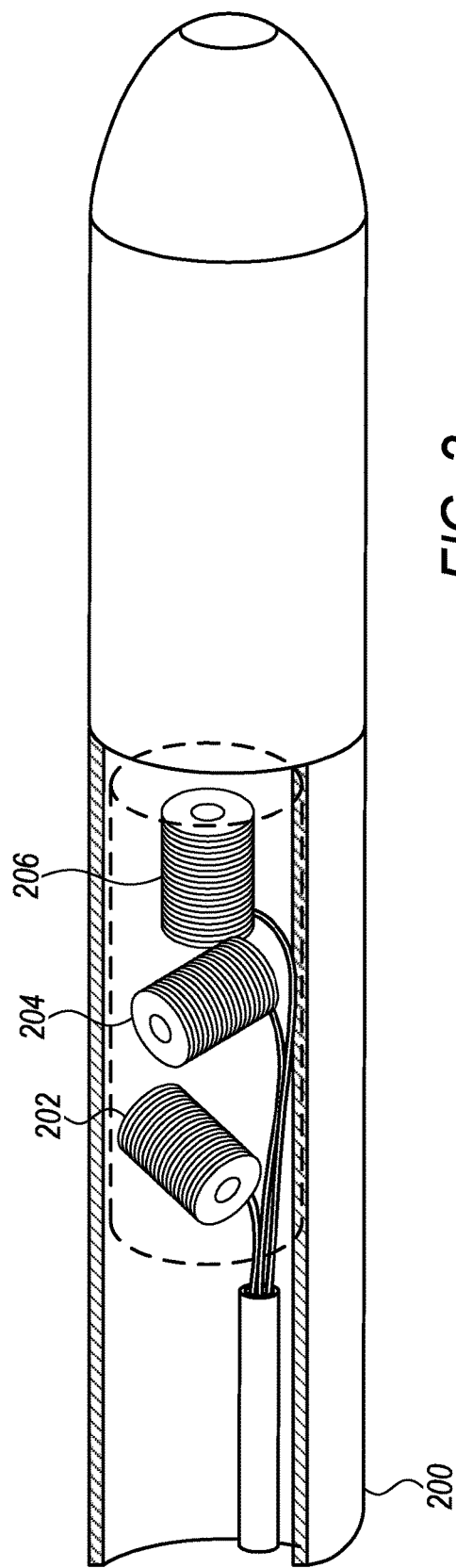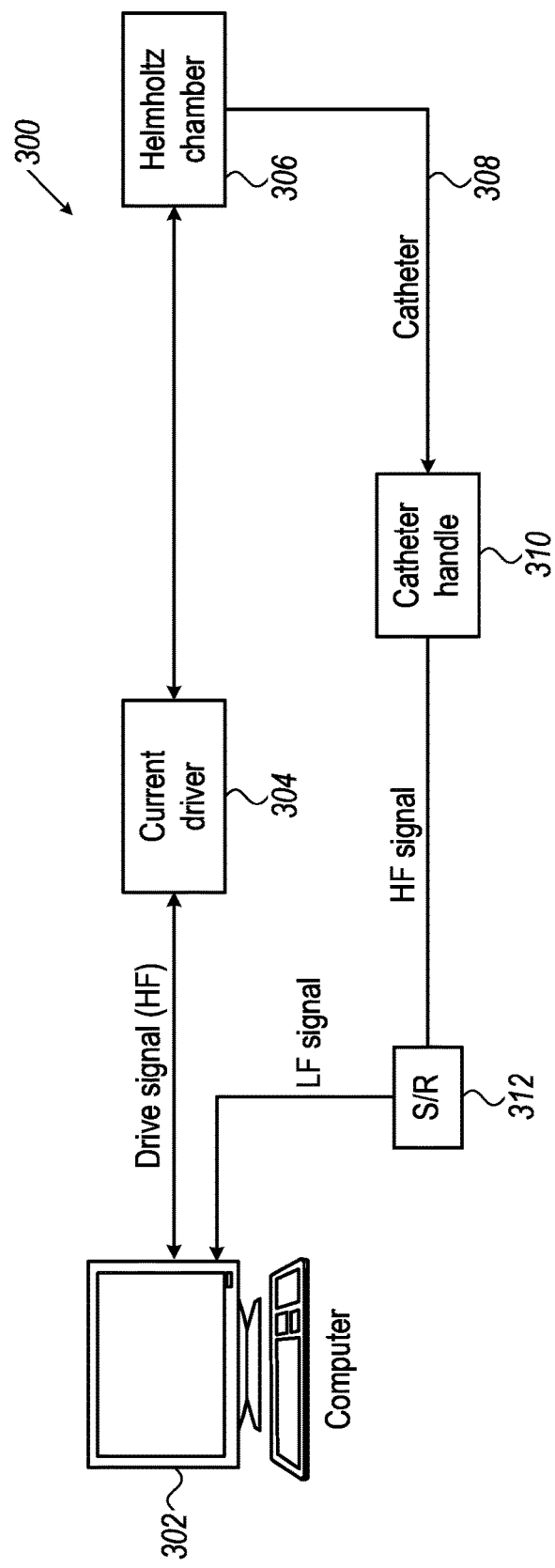

HETERODYNE CATHETER CALIBRATION SYSTEM

FIELD OF THE INVENTION

The present invention relates generally to medical diagnosis and treatment, and specifically to calibration of medical catheters whose location can be detected.

BACKGROUND OF THE INVENTION

Various methods and devices have been described for determining the position of a probe or catheter distal end inside the body using electromagnetic fields, such as in U.S. Pat. No. 5,042,486 and PCT International Publication WO 1994/004938. Other electromagnetic tracking Systems, not necessarily for medical applications, are described in U.S. Pat. Nos. 3,644,825, 3,868,565, 4,017,858, 4,054,881 and 4,849,692. PCT International Publication WO/1996/005768, which is assigned to the assignee of the present patent application, describes a catheter System including means for determining the Six-dimensions of position and orientation of the catheter's distal end. This System uses a plurality of non-concentric coils adjacent to a locatable site in the catheter, for example near its distal end. Preferably three orthogonal coils are used. These coils generate Signals in response to externally applied magnetic fields, which allow for the computation of six position and orientation coordinates, so that the position and orientation of the catheter are known without the need for imaging the catheter.

Lastly, U.S. Pat. No. 6,266,551, which is likewise assigned to the assignee of the present patent application, describes a catheter calibration and usage monitoring system, including a probe for insertion into a body of a subject, the probe having a distal end, and proximal end and a microcircuit that stores calibration information related to the probe. The microcircuit preferably stores and encrypted calibration code; alternatively, or additionally, the microcircuit stores a usage code, controlling the availability of the probe to a user.

SUMMARY OF THE INVENTION

An embodiment of the present invention provides a catheter calibration system including a calibration chamber, a receiver and a processor. The calibration chamber is configured to generate a calibration magnetic field that oscillates at a first frequency. The calibration chamber includes a cavity for inserting a distal end of a catheter having one or more magnetic-field sensors. The receiver is configured to be connected to the catheter that is inserted in the cavity of the calibration chamber, to receive from the catheter one or more signals, which are generated by the one or more magnetic-field sensors in response to the calibration magnetic field, and to convert the one or more signals into one or more respective intermediate frequency (IF) signals having a second frequency that is lower than the first frequency. The processor is configured to receive the one or more IF signals from the receiver and to calculate catheter navigation calibration data from the one or more IF signals.

In some embodiments, the processor is configured to calculate a location of the distal end of the catheter based on the one or more IF signals, and to calculate the catheter navigation calibration data responsively to the calculated location. In an embodiment, the receiver is configured to convert the one or more signals into the one or more IF signals by multiplying the one or more signals by a Local Oscillator (LO) signal.

In another embodiment, the receiver is configured to filter the one or more IF signals so as to filter-out the first frequency. In yet another embodiment, the processor is configured to operate in a low-frequency calibration mode, by (i) causing the calibration chamber to generate the calibration magnetic field at a third frequency that is lower than the first frequency, (ii) receiving the one or more signals directly from the catheter, and (iii) calculating the catheter navigation calibration data from the one or more signals received from the catheter at the third frequency.

There is additionally provided, in accordance with an embodiment of the present invention, a catheter calibration method including, in a calibration chamber that includes a cavity for inserting a distal end of a catheter having one or more magnetic-field sensors, generating a calibration magnetic field that oscillates at a first frequency.

One or more signals, which are generated by the one or more magnetic-field sensors in response to the calibration magnetic field, are received from the catheter that is inserted in the cavity of the calibration chamber. The one or more signals are converted into one or more respective intermediate frequency (IF) signals having a second frequency that is lower than the first frequency. Catheter navigation calibration data is calculated from the one or more IF signals.

The present invention will be more fully understood from the following detailed description of the embodiments thereof, taken together with the drawings in which:

BRIEF DESCRIPTION OF THE DRAWINGS

FIG. 2 is a block diagram that schematically illustrates navigation coils in a catheter distal end, in accordance with an embodiment of the present invention;

FIG. 3 is a block diagram that schematically illustrates a calibration system for High Frequency (HF) catheters, using a legacy calibration system, in accordance with an embodiment of the present invention;

DETAILED DESCRIPTION OF EMBODIMENTS

Overview

Figure 1:
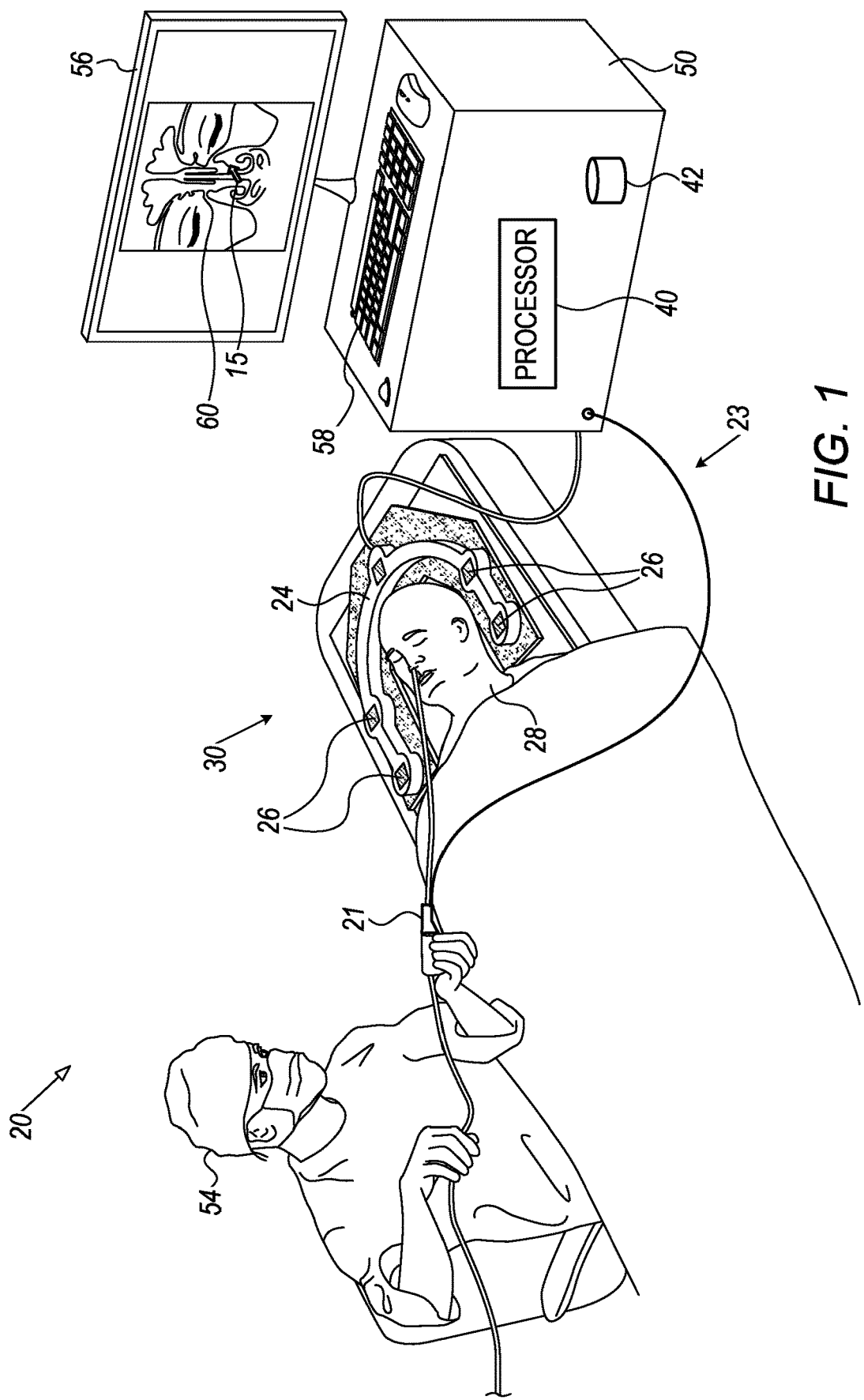
FIG. 1 is a schematic, pictorial illustration of an ear-nose-throat (ENT) system, in accordance with an embodiment of the present invention.

To facilitate catheter navigation in an intervascular procedure, the catheter distal end typically comprises a plurality (e.g., three or six) of coils; a magnetic field is generated at the procedure area, and the location (and, sometimes, the orientation) of the catheter distal end is derived by examining the currents that are induced in the coils in response to the magnetic field.

To calibrate the location and orientation measurement of the catheters, Helmholtz coil calibration chambers are typically used. Some legacy calibration chambers are designed to calibrate catheters wherein the frequency of the magnetic field is between 1-4 kHz. In an example calibration process, a known sinewave magnetic field is generated in the chamber, and the induced currents are sampled by software.

In a recent development, to reduce the size of the coils and allow more accurate tracking, catheters that operate at higher frequencies (e.g., 17-20 kHz) were introduced (will be referred to hereinbelow as High Frequency (HF) catheters). While this frequency is still below the Nyquist limit of the sampling circuit of the legacy calibration system, the accuracy of the calibration may degrade. For example, if a 4 kHz signal is sampled at 200K samples per second, there will be 50 samples in each cycle of the signal; however, if the same sampling frequency is used to sample a 20 kHz signal, there will be only 10 samples in each cycle, and the accuracy may degrade accordingly.

Embodiments according to the present invention provide apparatuses and methods that allow calibration of HF catheters using legacy calibration chambers and calibration hardware that were designed for lower frequency catheters. In embodiments, the induced current signals that the catheter outputs are multiplied by a locally generated sinewave signal (typically generated by a local oscillator) with a frequency that is close to the magnetic field frequency. For example, in an embodiment, the magnetic field frequency is 17 kHz, whereas the locally generated sinewave frequency is 16 kHz.

The multiplication of two sinewaves with frequencies f1, f2, is a superposition of two sinewaves—a first sinewave at a frequency that is equal to the sum of the two frequencies (f1+f2) ("the high frequency component" hereinbelow) and a second sinewave at a frequency that is equal to the difference f1−f2 of the two frequencies ("the low-frequency component"):

$$SIN(a)*SIN(b)=(COS(a-b)-COS(a+b))/2.$$

In some embodiments, a superheterodyne ("SuperHet") receiver is implemented. The SuperHet multiplies the HF signal that the HF catheter outputs responsively to the magnetic field in the calibration chamber (which oscillates at a first high frequency), by a second high frequency signal, wherein the difference between the two frequencies is significantly lower than either frequencies. The SuperHet then filters-off the high-frequency component and processes the low-frequency component only (the low-frequency component retains the amplitude (divided by 2) of the induced HF signal).

Returning to the example above, if a 20 kHz catheter signal is sampled at 200K samples per second (KSPS), there are only ten samples in each period. If a SuperHet is used, with a local-oscillator frequency of 18 kHz, the 2 kHz (20 kHz-18 kHz) low-frequency component will have 100 samples per period, increasing the signal processing accuracy.

In some embodiments, the SuperHet is implemented entirely by software. In alternative embodiments, a hardware SuperHet is employed.

The disclosed technique enables calibrating HF catheters using legacy calibration systems that were originally designed to calibrate low-frequency catheters, thereby saving considerable cost.

System Description

FIG. 1 is a schematic, pictorial illustration of an ear-nose-throat (ENT) system 20, in accordance with an embodiment of the present invention. In the following description an ENT catheter 21 in system 20 is assumed to be used to perform a suction procedure in the sinuses of a patient 28, although it will be understood that the tool may be used to perform other procedures on the patient.

In an embodiment, the distal end of catheter 21 comprises tools for various medical procedures, and tracking coils that generate induced current responsively to magnetic fields (the coils are described with reference to FIG. 2 below). For the tracking to be effective in system 20, frames of reference of a medical image 60, (e.g., a computerized tomography (CT) images of patient 28) are displayed on a screen 56.

Prior to and during the sinus procedure, a magnetic radiator assembly 24, comprised in the magnetic tracking system, is positioned beneath the patient's head. Assembly 24 comprises magnetic field radiators 26 which are fixed in position and which transmit alternating magnetic fields into a region 30 wherein the head of patient 28 is located. Currents generated by the coils in the catheter distal end, in response to the magnetic fields, enable the measurement of its position, direction, and angular orientation in the magnetic tracking system's frame of reference.

By way of example, five radiators 26 of assembly 24 are arranged in an approximately horseshoe shape around the head of patient 28. However, alternate configurations for the radiators of assembly 24 may be used, and all such configurations are assumed to be comprised within the scope of the present disclosure.

Elements of system 20 are under overall control of a system processor 40. Processor 40 may be mounted in a console 50, which comprises operating controls 58 that typically include a keypad and/or a pointing device such as a mouse or trackball. Console 50 connects to radiators 26 and to sensor 34 wirelessly and/or via one or more cables. A physician 54 uses operating controls 58 to interact with the processor while performing the ENT procedure using system 20. While performing the procedure, the processor presents a cursor 15 on medical image 60 on a screen 56 to assist the physician in guiding the distal end to a target tissue location in the sinuses.

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory.

Although the description hereinabove cited an ENT procedure, similar techniques may be used, mutatis mutandis, in inter-cardiac procedures; the magnetic field, in the case of a cardiac procedure, will be induced in a region wherein the heart of the patient is located.

In some embodiments, the position of the catheter distal end is typically measured using position sensing techniques. This method of position sensing is implemented, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

To accurately determine the position of the catheter distal end, the catheter should be calibrated using special catheter calibration equipment, which will be described further below.

FIG. 2 is a block diagram that schematically illustrates navigation coils in a catheter distal end 200, in accordance with an embodiment of the present invention. According to the example embodiment illustrated in FIG. 2, catheter distal end 200 comprises three coils that are perpendicular to each other: a first coil 202, a second coil 204 and a third coil 206. The coils are configured to generate induced currents responsively to the magnetic field (or, more precisely, to the first derivative of the magnetic field) in three orthogonal axes. The currents that the coils generate are coupled to electric wires, which are routed through the catheter to the interface circuitry of processor 40 (FIG. 1), which is configured to calculate the position of the catheter distal end responsively to the induced currents.

As would be appreciated, the catheter distal end structure illustrated in FIG. 2 and described above is cited merely by way of example; in alternative embodiments there may be additional coils (e.g., to measure the orientation of the catheter distal end). In embodiments, the catheter distal end may comprise filters that filter-off noise that may be generated by the coils. In some embodiments, the catheter (catheter distal end or elsewhere in the catheter) may comprise digitation circuitry, which converts the induced currents to digital form. In embodiments, some or all the coils are not necessarily perpendicular to other coils. In yet other embodiments, the catheter transmits the signals wirelessly.

The coils described above are magnetic field sensors. Other types of magnetic field sensors may be used in other embodiments, e.g., Hall-effect sensors.

Magnetic-Field Frequency and Calibration

Legacy catheter navigation systems use magnetic fields that oscillate in a low frequency range, e.g., between 1 to 4 kHz. Recently, however, new catheter navigation systems were introduced, that use a higher frequency magnetic field, e.g., 17 to 20 kHz. Higher frequency allows smaller coils, which may be advantageous, for example, in ENT procedures.

The catheter navigation system should be calibrated; in some embodiments the navigation system is calibrated once (e.g., prior to first use of a catheter); in other embodiments the navigation system is calibrated periodically, and in yet other embodiments calibration is done prior to each use. Calibration is typically done using calibration chambers, which are isolated from external magnetic fields (e.g., Helmholtz-coil calibration chambers). Legacy calibration chambers are suitable for calibrating catheters operating at the low frequency range, e.g., at frequencies of between 1 to 4 kHz.

In a typical catheter navigation calibration system, a computer generates a sinewave, which is converted to a magnetic field in the calibration system. The magnetic field is transmitted in the calibration chamber. Since the chamber is well isolated from the outside environment, the values (magnitudes and directions) of the magnetic field across the chamber are known with high accuracy. The catheter distal end is inserted in a dedicated cavity within the calibration chamber; the currents that are induced in the catheter distal end coils are amplified and then sampled by a sampling circuitry within the computer. The computer then calculates the location of the catheter distal end. Since the location of the distal end during calibration is known, calibration data may be accurately determined.

The accuracy requirement of the calibration process imposes a minimum sampling rate, depending on the frequency of the sampled signal. For example, to achieve some accuracy targets, each cycle of the signal must be sampled at least 50 times (according to the sampling theory, two samples per cycle are sufficient for accurate signal reconstruction; however, when noise is present, more samples may be needed).

Legacy calibration systems, which are large and expensive, are designed for the calibration of legacy catheters, which work at low frequencies such as between 1-4 kHz. The sampling rate of the legacy calibration system is, therefore, limited (e.g., to 200 KSPS). When such system is used for the calibration of an HF catheter, the number of samples per cycle may be insufficient. For example, if a 20 kHz signal (induced by a 20 kHz magnetic field) is sampled by a 200 KSPS sampler, only ten samples per cycles will be obtained. Moreover, the sampling aperture of a sampling circuit that is designed to sample a max-4 kHz signal may be too long for 20 kHz sampling (relative to the signal rate of change), resulting in unstable and/or noisy sampling.

In embodiments according to the present invention, a frequency mixing technique is used, enabling legacy calibration systems to calibrate HF catheters at high accuracy.

FIG. 3 is a block diagram that schematically illustrates a calibration system 300 for HF catheters, using a legacy calibration system, in accordance with an embodiment of the present invention. A computer 302 supplies a high frequency (HF) drive-signal to a current-driver circuit 304, which amplifies the current-drive signal and activates electromagnets that generate magnetic fields within a Helmholtz calibration chamber 306. The HF drive signal is typically in the range of 17-20 kHz.

The distal end 200 of an HF catheter 308 is inserted in Helmholtz calibration chamber 306. The magnetic field in the calibration chamber induces currents in navigation coils within the catheter distal end (e.g., coils 202, 204 and 206; FIG. 2). A Catheter Handle 310 in the proximal end of the catheter is coupled to a Signal Receiver 312, which converts the HF signals to low-frequency (LF) signals (e.g., in the range 1-4 kHz) and sends the LF signal back to computer 302. Computer 302 then analyzes the LF signals and, based on the LF signals and the driver signal, calculates the location of the catheter distal end. Since the location of the distal end during calibration is known, calibration data may be accurately determined.

As can be appreciated, the down-conversion of the HF signals into the LF signals does not change the amplitude characteristics of the signal. In other words, each LF signal has amplitude characteristics proportional to those of the corresponding HF signal, up to some known ratio (typically a ratio of 1:2). Therefore, the LF signals can be used for calibration, even though the actual magnetic field that is applied to the catheter, and the actual signals sensed by the catheter, are in the high frequency range.

In some embodiments, Signal Receiver 312 comprises a Super-Heterodyne (Superhet) receiver that uses frequency mixing (e.g., using signal multiplication) to convert the input HF signals to LF signals (Intermediate Frequency, or IF, in Superhet nomenclature).

In some embodiments, calibration system 300 is a legacy catheter calibration system that may be used for the calibration of legacy LF catheters, except that, for the calibration of HF catheters, a Superhet receiver is added.

Thus, by adding a Superhet receiver to a legacy calibration system, computer 302 can accurately derive the catheter distal end location by analyzing low frequency rather than high frequency signals.

As would be appreciated, the structure of calibration system 300 illustrated in FIG. 3 and described above is cited by way of example. Other suitable structure may be used in alternative embodiments. For example, in some embodiments, receiver 312 may be in computer 302, implemented by software, by hardware, or by combination of software and hardware. In some embodiments, the calibration chamber is configured to generate the magnetic field responsively to a digital signal that computer 302 generates, and current-drive 304 is not needed.

The embodiments described herein refer to a LF range of 1-4 kHz and a HF range of 17-20 kHz. This choice, however, is made purely by way of example. In alternative embodiments, the disclosed techniques can be used with any other suitable LF and HF ranges.

In some embodiments, Superhet receiver 312 converts each HF signal to a respective LF signal by multiplying the catheter output signal, which oscillates at a first frequency, by a locally generated sinewave oscillating at a second frequency (we will refer to a single catheter output signal, although each coil in the distal end of the catheter generates a separate signal; all such signals oscillate at the same frequency and are identically handled). According to basic trigonometry, the result of the multiplication is a superposition of a first signal having a frequency equal to the sum of the first and second frequencies, and a second signal having a frequency that is equal to the difference between the first and second frequencies:

$$SIN(a)*SIN(b)=(COS(a-b)-COS(a+b))/2.$$

Figure 4:
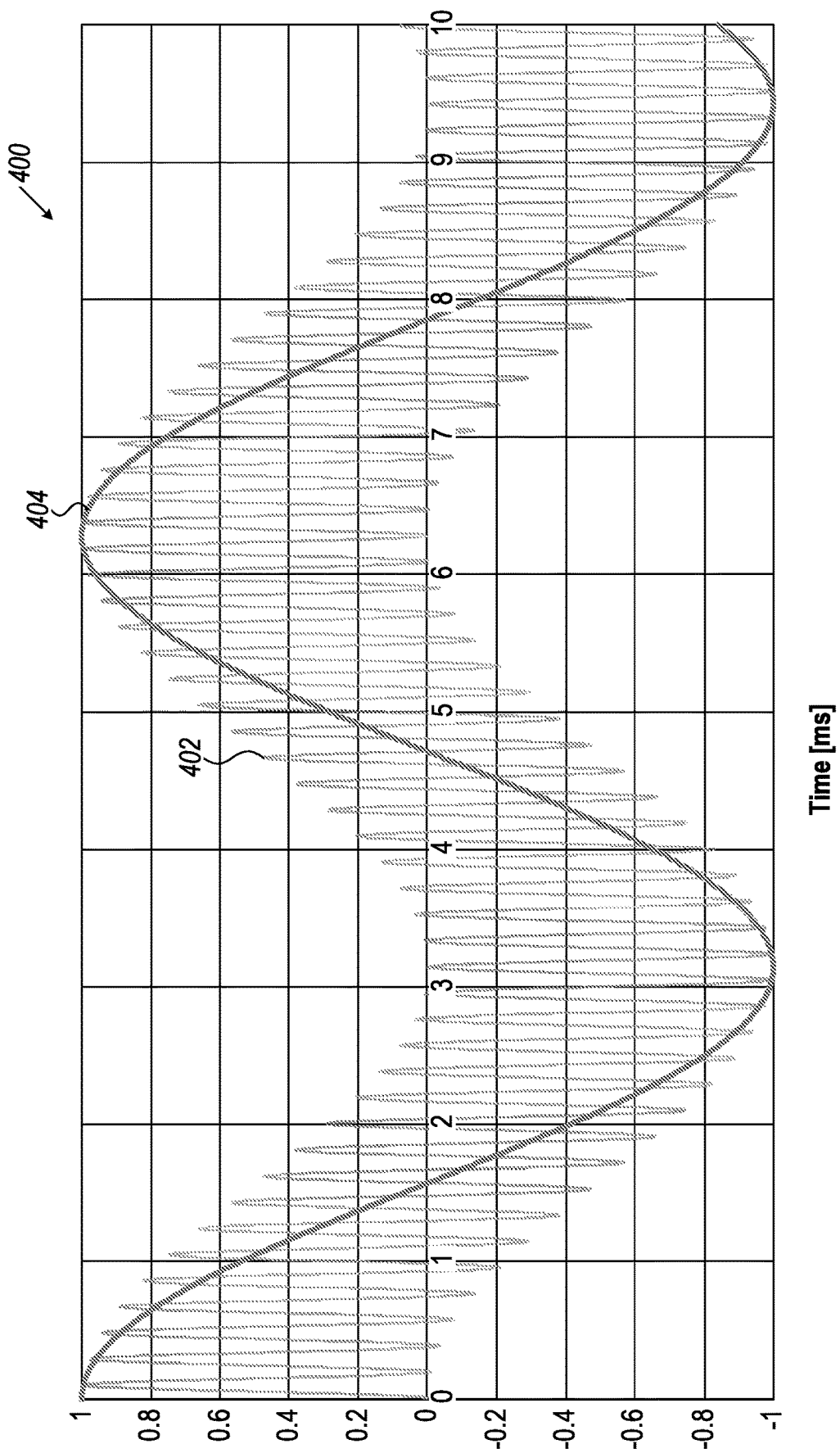
FIG. 4 is a graph that schematically illustrates multiplication of an induced sinewave that is generated by an HF catheter, by a sinewave that is generated in a Superheterodyne ("Superhet") local oscillator, in accordance with an embodiment of the present invention.

FIG. 4 is a graph 400 that schematically illustrates multiplication of an induced sinewave that is generated by an HF catheter, by a sinewave that is generated in a Superheterodyne local oscillator, in accordance with an embodiment of the present invention. According to the example embodiment illustrated in FIG. 4, the frequencies of the induced sinewave and the local oscillator sinewave are, respectively, 17,000 Hz and 16,000 Hz. The multiplication of the induced sinewave and the local oscillator sinewave is depicted by a curve 402. As can be observed, curve 402 comprises an HF component, with frequency equal to 17,000+16,000=33,000 Hz, and an LF component, depicted by a curve 404, with frequency 17,000−16,000=1,000 Hz.

In an embodiment, the HF component is filtered-off, and the LF component is forwarded to computer 302 (FIG. 3).

Embodiments Using Software Implementation

In some embodiments, the Superhet receiver is implemented by software, that is executed by a computer 302 (FIG. 3). The sampling circuit samples the HF signal that the HF catheter outputs, and the number of samples per cycles is relatively low; however, the LF frequency that is generated by multiplying the catheter HF frequency by a locally generated HF signal has a low frequency, with a sufficiently large number of samples per cycle.

Figure 5:
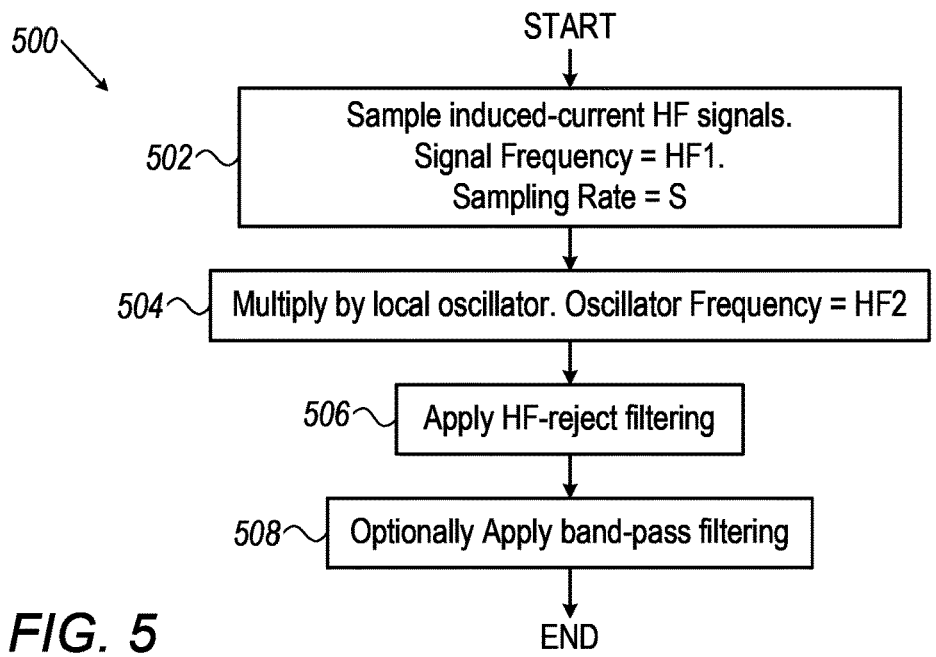
FIG. 5 is a flowchart that schematically illustrates a method for a Superhet receiver that is used for HF catheter calibration, in accordance with an embodiment of the present invention.

FIG. 5 is a flowchart 500 that schematically illustrates a method for a Superhet receiver that is used for HF catheter calibration, in accordance with an embodiment of the present invention. The flowchart is executed by computer 302, depicted in FIG. 3 (note that Superhet receiver 312 of FIG. 3 is replaced by a signal amplifier). In some embodiments, computer 302 may comprise a Digital Signal Processor (DSP).

The flowchart starts at a Sample Induced Current Signal step 502, wherein the computer samples the induced-currents signals that the catheter outputs. The frequency of the signals is HF1 (e.g., 17 kHz), and the sampling rate is S (e.g., 170 KSPS). The number of samples in each cycle of the sampled signal equals S/HF1 (10 for the exemplary numbers cited above), which may be insufficient for accurate determination of the catheter distal end location.

The computer next, in a Multiply-by-Local-Oscillator step 504, multiplies the samples by a sinewave with frequency HF2 (e.g., 16 kHz). As explained above, the result of the multiplication is a superposition of two signals—an HF signal having a frequency of HF1+HF2 (e.g., 33 kHz), and an LF signal having a frequency of HF1-HF2 (e.g., 1 kHz).

Next, in an HF-Reject step 506, the computer filters-off the HF signal. As the difference between the LF frequency (e.g., 1 kHz) and the HF frequency (e.g., 33 kHz) is large, a relatively simple filter may be used.

Next, in an optional Bandpass Filtering step 508, the computer may further reject any out-of-band noise from the signal, and send a clean LF signal for further legacy signal processing, which determines the location of the catheter distal end and the corresponding calibration data.

As would be appreciated, the flowchart illustrated in FIG. 5 and described herein is cited by way of example. Other suitable flowcharts may be used in alternative embodiments. For example, in some embodiments, Bandpass Filtering step 508 may be skipped; in other embodiments, HF-Reject step 506 may be skipped, as the bandpass filtering of step 508 also rejects the HF signal. The cited frequencies (and sample rates) are exemplary frequencies—any other suitable frequencies and sampling rates may be used in alternative embodiments.

Figure 6:
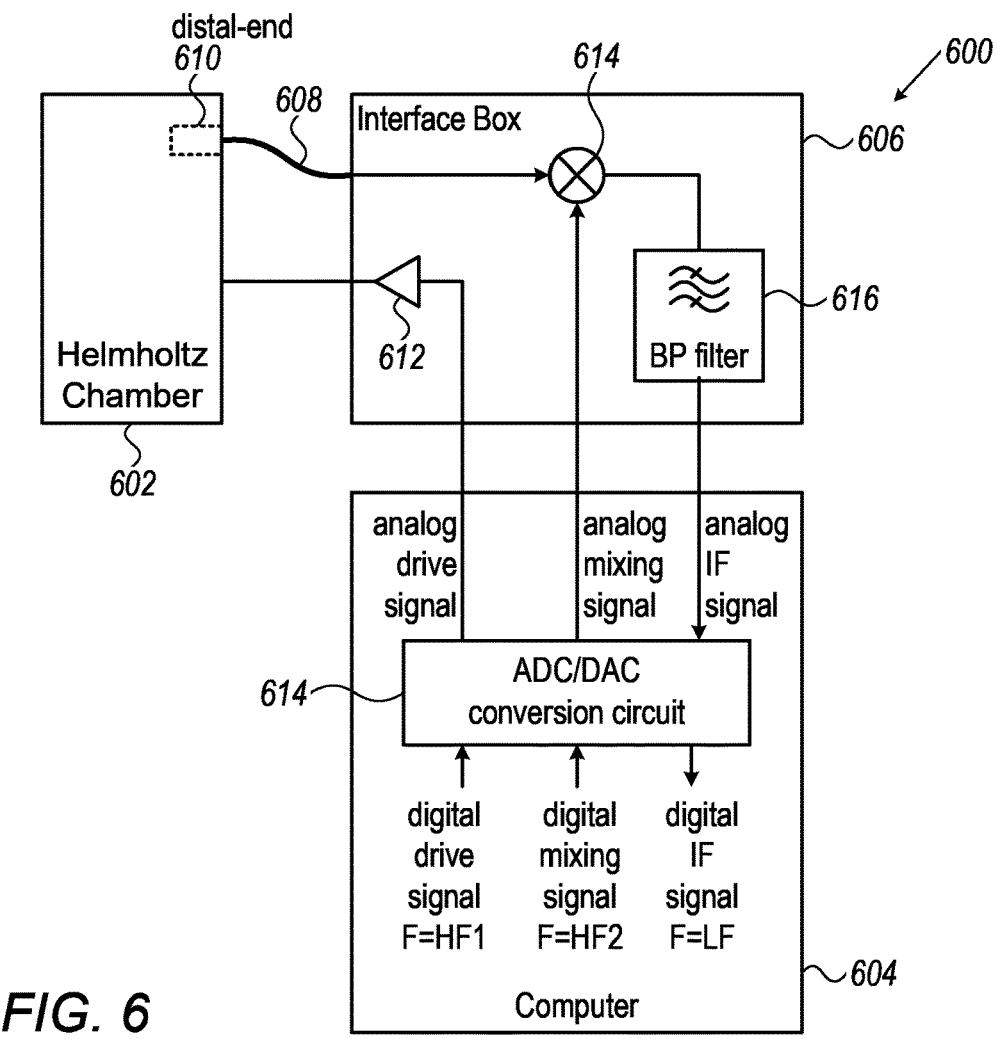
FIG. 6 is a block diagram that schematically illustrates a hardware Superhet HF catheter calibration system, in accordance with an embodiment of the present invention.

FIG. 6 is a block diagram that schematically illustrates a hardware super-het HF catheter calibration system 600, in accordance with an embodiment of the present invention. The system comprises a Helmholtz calibration chamber 602, a Computer 604 and an Interface Box 606. The distal end of an HF catheter 610 is inserted in a cavity in calibration chamber 602. The catheter outputs signals which correspond to currents induced in the calibration coils at the distal end of the catheter, to interface box 606.

Computer 604 comprises an ADC/DAC circuitry 614, which is configured to convert analog signals to digital samples and digital samples to analog signals.

Computer 604 generates digital samples of a sinewave drive signal at frequency HF1 (e.g., 17 kHz) and digital samples of a sinewave mixing signal at frequency HF2 (e.g., 16 kHz). The ADC/DAC circuitry converts the digital samples to an analog drive signal and an analog mixing signal.

According to the example embodiment illustrated in FIG. 6, the analog drive signal is amplified by a linear amplifier 612 in interface box 606, and then applied to the magnetic-field input of the calibration chamber, which generates a magnetic field proportional to the drive signal; in some embodiments, amplifier 612 is not required, and the analog drive signal is applied directly to the calibration chamber.

The distal end of catheter 608, which is inserted at a precisely measured location within calibration chamber 602, generates induced currents responsively to the magnetic field within the calibration chamber; the catheter outputs signals corresponding to the currents induced in the navigation coils (within the catheter distal end) to a signal multiplier 614 within interface box 606. In embodiments, any suitable analog signal multiplication technique may be used; see, for example, U.S. Pat. Nos. 5,442,583 and 6,810,240.

As explained above, the output of multiplier 614 is a superposition of two sinewaves—an HF sinewave with frequency HF1+HF2 and an LG sinewave with frequency HF1−HF2 (which is referred to as Intermediate Frequency signal, or IF signal, in Superhet nomenclature). Interface Box 606 further comprises a bandpass filter 616, which is configured to attenuate all frequencies except the difference HF1−HF2; in some embodiments bandpass filter 616 may comprise a resonator.

The IF signal is coupled to ADC/DAC conversion circuit 614, which converts the IF signal to digital samples at low frequency LF=HF1−HF2. The digital samples are then processed by computer 604, to determine a location correction value.

As would be appreciated, the structure of calibration system 600 illustrated in FIG. 6 and described herein is cited by way of example. Other suitable structures may be used in alternative embodiments. For example, in some embodiments, amplifier 612 is not needed. In an embodiment, calibration chamber 602 is configured to receive a digital signal that represents the magnetic field to be applied (and, in this case, the digital drive signal is wired directly from the computer to the calibration chamber).

Figure 7:
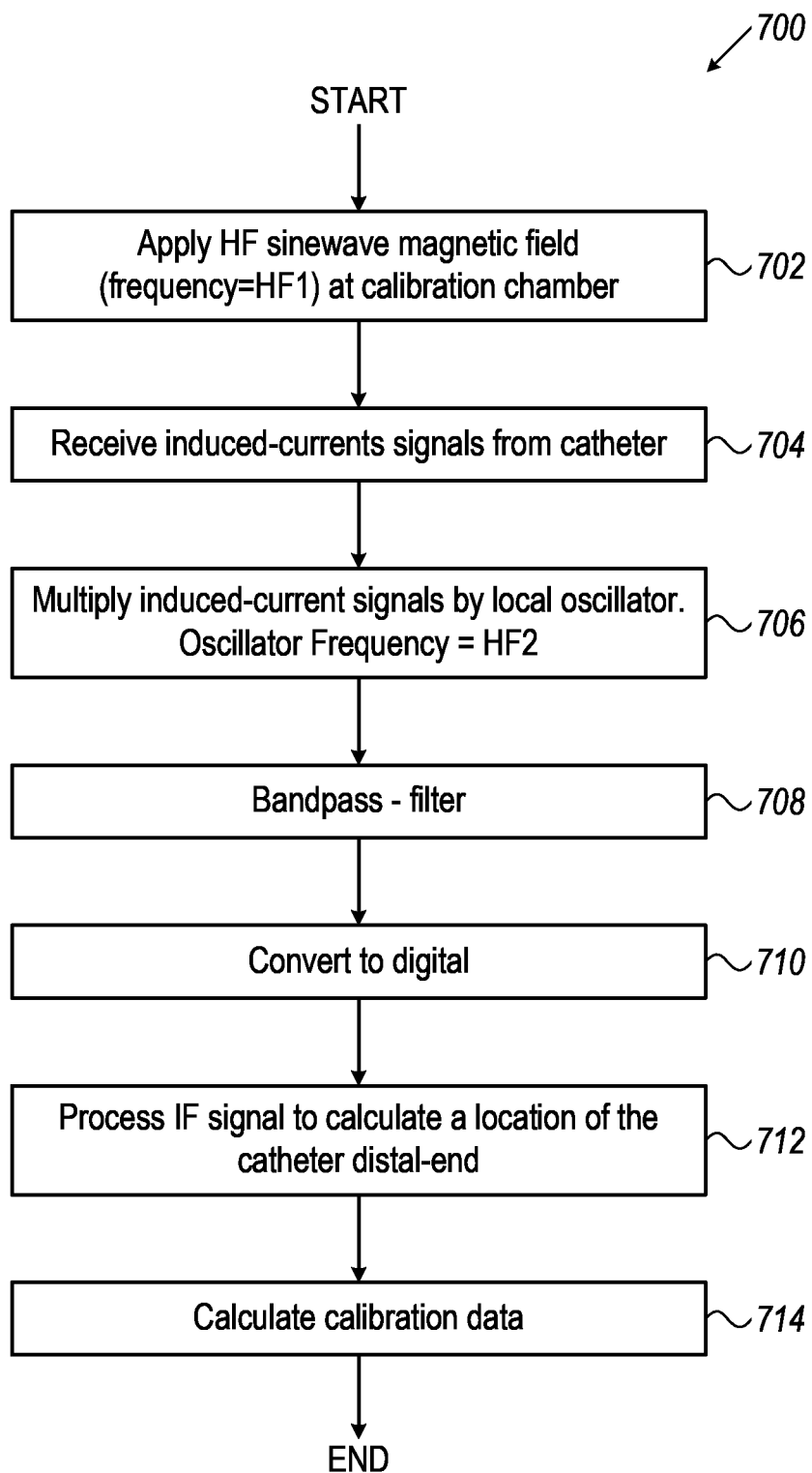
FIG. 7 is a flowchart that schematically illustrates a method for the calibration of HF catheters, using a hardware Superhet receiver, in accordance with an embodiment of the present invention.

FIG. 7 is a flowchart that schematically illustrates a method 700 for the calibration of HF catheters using a hardware Superhet receiver, in accordance with an embodiment of the present invention. the flowchart is executed by various elements of a calibration system, e.g., system 600 (FIG. 6).

The flowchart starts at an Apply Magnetic Field step 702, wherein the calibration system applies a sinewave magnetic field within the calibration chamber. The frequency of the sinewave is HF1 (e.g., 16 kHz). Next, at a Receive Induced-Currents Signals 704, signals generated by the catheter, responsive to induced currents in the catheter coils, are input by an interface box of the calibration system. In a Multiply Signals step 706, an analog multiplier multiplies the signals output by the catheter by a sinewave signal at frequency HF2 (e.g., 17 kHz) that is generated by a local oscillator in the interface box. As explained above, the product signal comprises a signal with frequency HF1+HF2 and an IF signal with frequency HF1−HF2.

In a Bandpass-Filter step 708, a bandpass filter filters off the higher frequency signal, as well as noise that is outside the HF1−HF2 frequency band. The low-pass filtered signal is then converted, in a Convert-to-Digital step 710, to digital samples. Next, in a Process IF signal step 712, computer 604 digitally processes the IF signal and calculates the location of the catheter distal end. Lastly, in a Calculate Calibration Data step 714, the computer compares the calculated location of the catheter distal end to the accurate location and determines the calibration data. After step 714 the calibration flowchart ends.

As would be appreciated, the flowchart illustrated in FIG. 7 and described herein is cited by way of example. Other flowcharts may be used in alternative embodiments. For example, Bandpass-filter step 708 may be replaced (or augmented) by an HF-reject step, which attenuates the high frequency component.

The configuration of the calibration system and the calibration methods, including units and sub-units thereof, illustrated in FIGS. 1 through 7, are example configurations and methods that are depicted purely for the sake of conceptual clarity. Any other suitable configurations and methods can be used in alternative embodiments. The different system elements may be implemented using suitable hardware, such as in one or more Application-Specific Integrated Circuit (ASIC) or Field-Programmable Gate Arrays (FPGA) and/or discrete analog and mixed-signal components, using software, or using a combination of hardware and software elements.

Each of the described computers, such as processor 40 (FIG. 1), computer 302 (FIG. 3) and computer 614 (FIG. 6) typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In some embodiments some or all the computers may comprise digital signal processing (DSP) circuitry.

Although the embodiments described herein mainly address HF catheter calibration, the methods and systems described herein can also be used in other applications.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A catheter calibration system, comprising:
   a calibration chamber, configured to generate a calibration magnetic field that oscillates at a first frequency, the calibration chamber comprising a cavity for inserting a distal end of a catheter having one or more magnetic-field sensors;
   a receiver, which is configured to be connected to the catheter that is inserted in the cavity of the calibration chamber, to receive from the catheter one or more signals, which are generated by the one or more magnetic-field sensors in response to the calibration magnetic field, and to convert the one or more signals into one or more respective intermediate frequency (IF) signals having a second frequency that is lower than the first frequency, and wherein the receiver is further configured to convert the one or more signals into the one or more IF signals by multiplying the one or more signals by a Local Oscillator (LO) signal; and
   a processor, which is configured to receive the one or more IF signals from the receiver and to calculate catheter navigation calibration data from the one or more IF signals.

2. The catheter calibration system according to claim 1, wherein the processor is configured to calculate a location of the distal end of the catheter based on the one or more IF signals, and to calculate the catheter navigation calibration data responsively to the calculated location.

3. The catheter calibration system according to claim 1, wherein the receiver is configured to filter the one or more IF signals so as to filter-out the first frequency.

4. The catheter calibration system according to claim 1, wherein the processor is configured to operate in a low-frequency calibration mode, by:

causing the calibration chamber to generate the calibration magnetic field at a third frequency that is lower than the first frequency;

receiving the one or more signals directly from the catheter; and calculating the catheter navigation calibration data from the one or more signals received from the catheter at the third frequency.

5. A catheter calibration method, comprising:

in a calibration chamber that comprises a cavity for inserting a distal end of a catheter having one or more magnetic-field sensors, generating a calibration magnetic field that oscillates at a first frequency, receiving, from the catheter that is inserted in the cavity of the calibration chamber, one or more signals that are generated by the one or more magnetic-field sensors in response to the calibration magnetic field;

converting the one or more signals into one or more respective intermediate frequency (IF) signals having a second frequency that is lower than the first frequency, and wherein converting the one or more signals into the one or more IF signals comprises multiplying the one or more signals by a Local Oscillator (LO) signal; and calculating catheter navigation calibration data from the one or more IF signals.

6. The catheter calibration method according to claim 5, wherein calculating the catheter navigation calibration data comprises calculating a location of the distal end of the catheter based on the one or more IF signals, and calculating the catheter navigation calibration data responsively to the calculated location.

7. The catheter calibration method according to claim 5, wherein converting the one or more signals into the one or more IF signals comprises filtering the one or more IF signals so as to filter-out the first frequency.

8. The catheter calibration method according to claim 5, further comprising operating in a low-frequency calibration mode, by:

causing the calibration chamber to generate the calibration magnetic field at a third frequency that is lower than the first frequency;

receiving the one or more signals directly from the catheter; and calculating the catheter navigation calibration data from the one or more signals received from the catheter at the third frequency.

* * * * *